US009594057B2

(12) United States Patent
DiFoggio (10) Patent No.: US 9,594,057 B2
(45) Date of Patent: Mar. 14, 2017

(54) REFLECTION-ONLY SENSOR FOR FLUID ACOUSTIC IMPEDANCE, SOUND SPEED, AND DENSITY

(71) Applicant: Baker Hughes Incorporated, Houston, TX (US)

(72) Inventor: Rocco DiFoggio, Houston, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 261 days.

(21) Appl. No.: 14/160,084

(22) Filed: Jan. 21, 2014

(65) Prior Publication Data

US 2015/0204819 A1    Jul. 23, 2015

(51) Int. Cl.
*G01N 29/028* (2006.01)
*E21B 47/10* (2012.01)
*G01N 29/024* (2006.01)

(52) U.S. Cl.
CPC ......... *G01N 29/028* (2013.01); *E21B 47/101* (2013.01); *G01N 29/024* (2013.01); *G01N 2291/02818* (2013.01); *G01N 2291/044* (2013.01)

(58) Field of Classification Search
CPC ........................... G01N 29/024; G01N 29/028
USPC ...................................................... 73/152.58
See application file for complete search history.

(56) References Cited

U.S. PATENT DOCUMENTS

| | | | |
|---|---|---|---|
| 3,915,018 A | 10/1975 | Karplus | |
| 4,709,357 A | 11/1987 | Maki, Jr. | |
| 7,024,917 B2 | 4/2006 | DiFoggio | |
| 7,614,302 B2 | 11/2009 | DiFoggio et al. | |
| 2005/0259512 A1 | 11/2005 | Mandal | |
| 2007/0022803 A1 | 2/2007 | DiFoggio et al. | |
| 2009/0266165 A1 | 10/2009 | Greenwood | |
| 2010/0246325 A1 | 9/2010 | Egerev et al. | |
| 2013/0090561 A1* | 4/2013 | Kusukame | A61B 8/14 600/443 |

OTHER PUBLICATIONS

Int'l Search Report and Written Opinion in PCT/US2015/011141, dated Apr. 27, 2015.

* cited by examiner

*Primary Examiner* — Laura Martin
*Assistant Examiner* — Irving A Campbell
(74) *Attorney, Agent, or Firm* — Mossman Kumar & Tyler PC

(57) ABSTRACT

Methods, systems, and devices for estimating a parameter of interest of a downhole fluid. Methods may include using at least two solid acoustic transmission media, including a first media and a second media having different acoustic impedances and each having a corresponding face immersed in the downhole fluid. Methods may include using a reflection of an acoustic pulse from a solid-liquid interface at the corresponding face of the first media and the second media to estimate the parameter of interest. The sound speed and the acoustic impedance of the first media and the sound speed and the acoustic impedance of the second media may each be different than a sound speed and an acoustic impedance of the fluid and each other. The parameter of interest may be estimated independently of a time of flight in the downhole fluid of any acoustic pulses.

14 Claims, 4 Drawing Sheets

REFLECTION-ONLY SENSOR FOR FLUID ACOUSTIC IMPEDANCE, SOUND SPEED, AND DENSITY

FIELD OF THE DISCLOSURE

This disclosure generally relates to borehole tools, and in particular to methods and apparatuses for estimating a parameter of interest of a downhole fluid.

BACKGROUND OF THE DISCLOSURE

Determining the acoustic properties of downhole fluids may be desirable for several types of downhole evaluation. Such properties may be used in characterizing the fluid itself, or for use in methods for evaluating the formation, the borehole, the casing, the cement, or for previous or ongoing operations in the borehole including exploration, development, or production.

As one example, it is known to conduct acoustic inspection of a casing cemented in a borehole to determine specific properties related to the casing and surrounding materials. For example, the bond between the cement and the casing may be evaluated, or the strength of the cement behind the casing or the casing thickness may be estimated using measurements of reflected acoustic waves, which may be generally referred to as casing cement bond logging. For many of these techniques, it is desirable that variations in fluids filling the borehole (e.g., drilling fluid) be compensated for, because conventional processing is highly sensitive to the properties of the drilling fluid.

Thus, various techniques are currently employed to determine parameters of the fluid affecting acoustic measurements, such as acoustic impedance and sound speed in order to interpret the acoustic reflection data. Traditionally, time of flight of the acoustic signals has been used to determine sound speed, and additional measurements may be used to estimate at least one of acoustic impedance and density of the fluid.

SUMMARY OF THE DISCLOSURE

In aspects, the present disclosure is related to methods and apparatuses for estimating at least one parameter of interest of a downhole fluid relating to an earth formation intersected by a borehole.

One general method embodiment according to the present disclosure may include estimating at least one parameter of interest of a downhole fluid using an acoustic assembly comprising at least two solid acoustic transmission media, wherein a first media of the at least two solid acoustic transmission media has an acoustic impedance that is different than an acoustic impedance of a second media of the at least two solid acoustic transmission media, and wherein the first media and the second media each have a corresponding face immersed in the downhole fluid whose acoustic impedance is not the same as either of the solid media. Methods may include using a reflection of an acoustic pulse from a solid-liquid interface at the corresponding face of the first media and of the second media to estimate the parameter of interest. The acoustic pulse may be propagated within the at least two solid acoustic transmission media. The first media has a sound speed that is different than a sound speed of the second media, which are both different from the sound speed of the drilling fluid. The sound speed and the acoustic impedance of the first media and the sound speed and the acoustic impedance of the second media are both different than the sound speed and acoustic impedance of the fluid.

Methods may include estimating the parameter of interest independently of a time of flight in the downhole fluid of the acoustic pulse and any other acoustic pulses. Methods may include transmitting the acoustic pulse into the solid media using an acoustic transducer. Methods may include using the acoustic transducer to transmit the acoustic pulse into the solid media through a corresponding second face of each of the first media and the second media. The acoustic pulse may be transmitted through the corresponding second face of each of the first media and the second media simultaneously.

The second face may not be in contact with the borehole fluid. The acoustic transducer may not be in contact with the borehole fluid. The acoustic transducer may comprise a single acoustic transducer, and methods may include transmitting the acoustic pulse using only the single acoustic transducer. The acoustic assembly may include a substantially right circular cylinder. Each of the first media and the second media may comprises a substantially half-cylinder and wherein each face comprises a semicircle. The parameter of interest may be at least one of: i) sound speed of the downhole fluid; ii) acoustic impedance of the downhole fluid; and iii) density of the downhole fluid.

Apparatus embodiments may include a carrier configured to be conveyed into a borehole; a logging tool mounted on the carrier, the logging tool including an acoustic assembly comprising at least two solid acoustic transmission media, wherein a first media of the at least two solid acoustic transmission media has an acoustic impedance that is different than an acoustic impedance of a second media of the at least two solid acoustic transmission media, and wherein the logging tool is configured such that when the borehole is filled with downhole fluid, the first media and the second media each have a corresponding face immersed in the downhole fluid; and a processor configured to use a reflection of an acoustic pulse from the solid-liquid interface at the corresponding face of the first media and the second media to estimate the parameter of interest. The apparatus may be further configured to carry out method embodiments as described herein. For example, the processor may be configured to carry out the methods described above.

Further embodiments may include a non-transitory computer-readable medium product having instructions thereon that, when executed, cause at least one processor to perform a method as described above. The non-transitory computer-readable medium product may include at least one of: (i) a ROM, (ii) an EPROM, (iii) an EEPROM, (iv) a flash memory, or (v) an optical disk.

Examples of some features of the disclosure may be summarized rather broadly herein in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION

In aspects, this disclosure relates to estimating a parameter of interest of a downhole fluid in an earth formation intersected by a borehole. The at least one parameter of interest may include, but is not limited to, one or more of: (i) sound speed of the fluid, (ii) acoustic impedance of the fluid, (iii) density of the fluid.

Various techniques have been used to analyze downhole fluids. Such techniques may include the use of instruments for obtaining information relating to a parameter of interest in conjunction with sample chambers storing the sampled fluid for analysis or sample chambers allowing the fluid to pass through (continuously, or as directed by a flow control) for sampling, or as mounted on an exterior of a tool body of a downhole tool. Example systems may use a signal generator and sensor (which may be combined; e.g., a transducer) for determining acoustic impedance. In the well-known time of flight method, the sound speed, c, of a fluid may be determined by dividing the travel time of the signal through the fluid by the distance the signal traveled through the fluid.

It would be desirable to reduce the size of the measurement apparatus on a downhole tool, particularly Measurement-While-Drilling ('MWD') and Logging-While-Tripping ('LWT') tools. Design considerations for instruments used in MWD and LWT tools are particularly demanding in terms of dimensional specifications. Various tradeoffs may be accepted in terms of design. As one example, a smaller sensor may be obtained by using a higher frequency transducer, but drilling fluids tend to be full of particles that cause dramatic signal attenuation in the fluid with increasing frequency. For particle-laden drilling fluid, according to particular configurations, an upper limit for frequency may be 250 kHz or 500 kHz for transmission with acceptable attenuation through approximately 25 mm of drilling mud. Thus, configuring a traditional time-of-flight instrument for use in an MWD or LWT tool or in other space-restrictive downhole applications can be problematic depending upon the drilling fluid. Traditional methods may include placing a transducer on one face of a solid cylinder ('buffer rod') and placing the other face in contact with the fluid to allow estimation of fluid impedance, but that approach would also require a memorized calibration in air at the surface rather than a downhole calibration.

Aspects of the present disclosure include a reflection-only instrument for estimating downhole fluid (e.g., drilling fluid) acoustic impedance, sound speed, and density; time-of-flight analysis may thus be avoided with this instrument. An acoustic transducer may be placed across a seam on the face of a cylinder split along its axis, wherein each half cylinder may have a different acoustic impedance and/or sound speed. Fluid impedance is determined from the ratio of the perpendicular reflection intensities of each half, which makes the sensor self-calibrating downhole. Two other acoustic transducers may be placed on the sides of each half cylinder at an angle relative to their fluid-immersed end faces to make use of the fact that glancing reflection intensity depends on both sound speed and impedance. In this way, fluid sound speed can be determined from the two glancing reflection intensities without ever making any measurements upon any sound waves that might be transmitted into the fluid. That is, there may be no acoustic pulse transmitted through the fluid, or the transmitted pulse may be ignored (e.g., not measured). Therefore, very small, high-frequency transducers may be used without any concern about the acoustic attenuation of the drilling fluid. Fluid density may be obtained by dividing the fluid acoustic impedance by the fluid sound speed.

Device embodiments may include an acoustic assembly comprising at least two solid acoustic transmission media, wherein a first media of the at least two solid acoustic transmission media has an acoustic impedance that is different than an acoustic impedance of a second media of the at least two solid acoustic transmission media. Method embodiments may include determining a parameter of interest of a downhole fluid using the acoustic assembly, wherein the first media and the second media each have a corresponding face immersed in the downhole fluid. Methods may include using a reflection of an acoustic pulse from a solid-liquid interface at the corresponding face of the first media and the second media to estimate the parameter of interest.

Figure 1A:
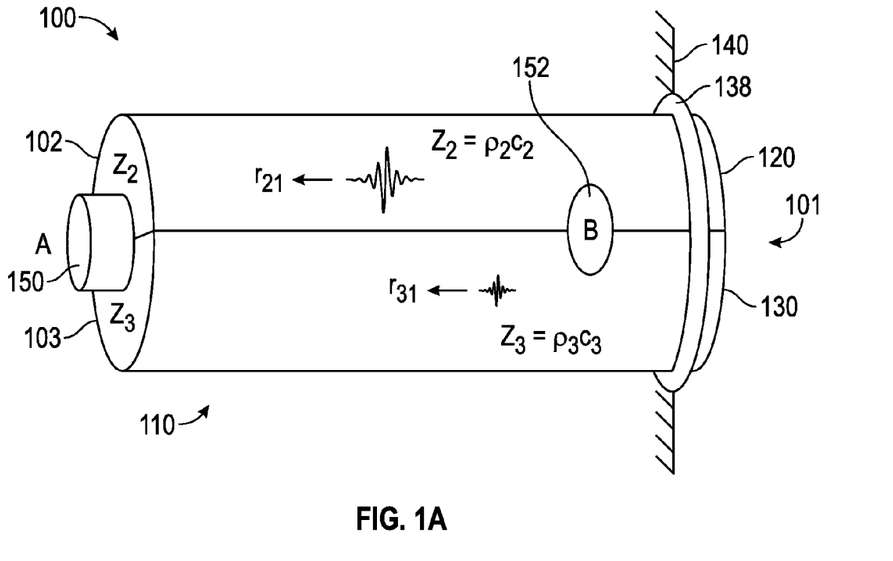
FIGS. 1A and 1B show a device in accordance with embodiments of the present disclosure.
Figure 1B:
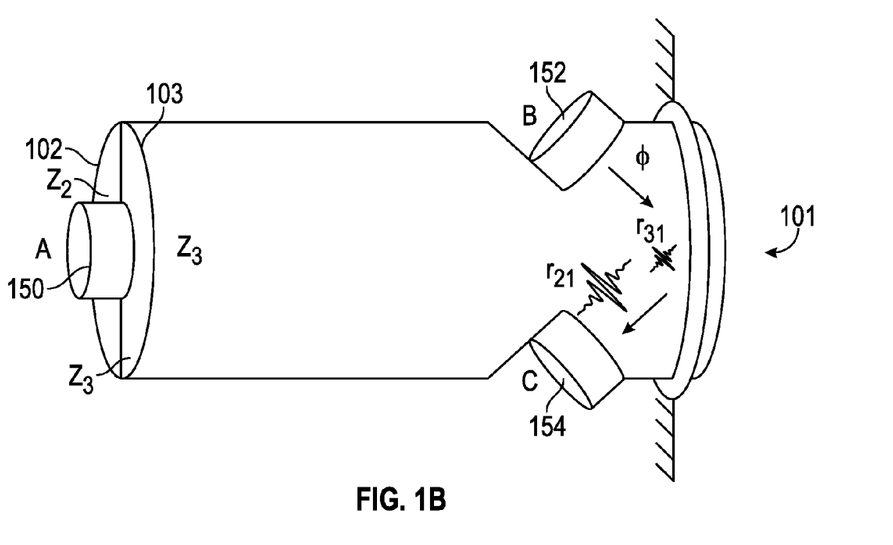

FIGS. 1A and 1B show a device in accordance with embodiments of the present disclosure. The perspective of FIG. 1A is offset 90 degrees from that of FIG. 1B. The device 100 comprises an acoustic assembly 110 which includes two acoustic transmission media 102 and 103 made of different materials. The media may each be solid media, i.e., a media that when unconstrained holds its shape for at least the near term. Alternate embodiments may include more than two media. At a first end of the first and second media 102, 103 (proximate the fluid) is a corresponding face (120 and 130, respectively) of the media 102, 103. The device 100 is configured so that each corresponding face is immersed in the borehole fluid 101 for operation.

An acoustic transducer 150 is positioned at an end of the media opposing the first end, and configured to provide an acoustic pulse (not shown) that propagates within the two media 102, 103. The acoustic transducer may be positioned so that it is located half on one media and half on the other, equally straddling the boundary between them.

Transducer 150 is configured to provide an acoustic pulse (not shown) normal to the corresponding face (120, 130) of the first media 102 and the second media 103 and to receive the reflection of the pulse (having reflected amplitudes, $r_{21}$ and $r_{31}$, respectively) from the solid-liquid interface at the corresponding face of the first media 102 and the second media 103. In this example, transducer 150 may serve as transmitter and receiver, however, in some embodiments, the role of transmitter may be performed by a device other than transducer 150.

Referring to FIG. 1B, an acoustic source (transducer 152) is configured to provide a non-normal incidence acoustic pulse to the the corresponding face of the first media and the second media. A receiver (transducer 154) is configured to receive the reflection of the non-normal pulse from the solid-liquid interface. Transducers 150-154 may be any appropriate transducer, such as, for example, piezoelectric transducers, magnetostrictive transducers, and so on, as will occur to one of skill in the art.

The first media 102 has an acoustic impedance ($Z_2$) that is different than an acoustic impedance ($Z_3$) of the second media 103. In the present example, the first media 102 also has a sound speed ($c_2$) that is different than a sound speed ($c_3$) of the second media 103. Further, in this example the sound speed and the acoustic impedance of the first media 102 and the sound speed and the acoustic impedance of the second media 103 are each different than a sound speed ($c_1$) and an acoustic impedance ($Z_1$) of the fluid 101.

In operation, we can now calculate the acoustic impedance of the fluid from the ratio of the reflected amplitudes. The reflected pulses are distinguishable from each other because they return at different times because the sound speeds of the first and second media are different. Alternatively, if the two media had the same sound speed, then the media would have to be of unequal lengths for the reflected pulses to be distinguished in time.

The acoustic impedance, Z, of a material is its density times its sound speed. For a perpendicular reflection from the interface, we may use the well-known reflection amplitude for a sound wave going from the second media 102 to the first media (fluid 101), that is given by $r_{21}=(Z_2-Z_1)/(Z_2+Z_1)$. Similarly, going from Medium 3 to Medium 1 the reflection amplitude is $r_{31}=(Z_3-Z_1)/(Z_3+Z_1)$. In the case that media 102 and 103 are side by side, with their far ends immersed in the fluid (medium 1) and transducer 150 placed as above, then it is possible to calculate the acoustic impedance of the fluid from the ratio of the reflection amplitudes, namely, by solving for $Z_1$ by dividing the equation for $r_{21}(Z_1,Z_2)$ by the equation for $r_{31}(Z_1,Z_3)$. By dividing numerator and denominator of Eq. 1 by $r_{31}$, it is clear that $Z_1$ depends only upon the ratio, $r_{21}/r_{31}$.

$$r_{21}/r_{31}=[(Z_1-Z_2)/(Z_1+Z_2)]/[(Z_1-Z_3)/(Z_1+Z_3)]$$

$$Z_1=\{-(r_{21}+r_{31})(Z_2-Z_3)\pm\mathrm{Sqrt}\;[(r_{21}+r_{31})^2(Z_2-Z_3)^2+4(r_{21}-r_{31})^2 Z_2 Z_3]\}/[2(r_{21}-r_{31})] \quad \text{Eq. 1}$$

For a glancing (non-perpendicular) reflection of a wave starting in the second medium 102 and going towards the fluid 101 at an angle, $\phi$, to the interface, $$r_{21}=[(Z_1/Z_2)\sin\phi - \mathrm{Sqrt}(1-(c_1/c_2)^2\cos^2\phi)]/[(Z_1/Z_2)\sin\phi + \mathrm{Sqrt}(1-(c_1/c_2)^2\cos^2\phi)]$$

Solving for $Z_1$, $$Z_1=[Z_2/\sin\phi][(1+r_{21})/(1-r_{21})]\;\mathrm{Sqrt}\;[1-(c_1/c_2)^2\cos^2\phi] \quad \text{Eq. 2}$$

For a glancing (non-perpendicular) reflection of a wave starting in the third medium 103 and going towards the fluid 101 at an angle, $\phi$, to the interface, $$r_{31}=[(Z_1/Z_3)\sin\phi - \mathrm{Sqrt}(1-(c_1/c_3)^2\cos^2\phi)]/[(Z_1/Z_3)\sin\phi + \mathrm{Sqrt}(1-(c_1/c_3)^2\cos^2\phi)]$$

Solving for $Z_1$, $$Z_1=[Z_3/\sin\alpha][(1+r_{31})/(1-r_{31})]\;\mathrm{Sqrt}\;[1-(c_1/c_3)^2\cos^2\phi] \quad \text{Eq. 3}$$

The assembly is configured to use transducer 132 to transmit a pulse striking the interface at a non-normal angle. By equating the expression for $Z_1$ in Eq. 2 to the expression for $Z_1$ in Eq. 3, we can eliminate $Z_1$ and we can solve for $c_1^2$, $$c_1^2=[1-\{(Z_3/Z_2)[(1+r_{31})(1-r_{21})]/[(1-r_{31})(1+r_{21})]\}^2]/\cos^2\phi\{[(1/c_2)^2-((1/c_3)^2\{(Z_3/Z_2)[(1+r_{31})(1-r_{21})]/[(1-r_{31})(1+r_{21})]\}^2]\} \quad \text{Eq. 4}$$

Dividing the fluid acoustic impedance by the fluid sound speed, the fluid density may be obtained as shown in Eq. 5. Because the sound speed may be determined from off-normal reflection measurements, a time of flight measurement of an acoustic pulse through the fluid may be avoided.

$$\rho_1=Z_1/c_1 \quad \text{Eq. 5}$$

Returning to FIG. 1, device 100 is configured such that corresponding faces 120, 130 of the acoustic assembly 110 are immersed in the downhole fluid, but the bulk of the device is not in contact with fluid. The corresponding opposite ends of media 102, 103 across from the corresponding faces 120, 130 are not in contact with the fluid, nor is transducer 150. For example, seal 138 between device 100 and the tool body 140 of a logging tool (as described herein with respect to FIGS. 2 and 3) may isolate the bulk of the device from downhole fluid 101.

As shown, device 100 may be positioned substantially flush with the tool body 140. Thus, in some embodiments, corresponding faces 120, 130 may be on an outer surface of the tool, such as a drill string, such that a sample chamber is not required. The substantially flush configuration reduces the likelihood of pack off (clogging by drilling mud solids) because the face is substantially the only part of the instrument in contact with the drilling fluid. In other embodiments, the device may be configured for use in a sample chamber. The reflection-only aspects of the present disclosure enable use in size restrictive applications and allow use of higher acoustic frequencies.

The acoustic assembly 110 may be a substantially right circular cylinder as shown in FIG. 1. Each of the first media 102 and the second media 103 may be substantially a half-cylinder. That is, the interface between adjacent faces of the first media 102 and the second media 103 may bisect the substantial cylindrical acoustic assembly 110 through its longitudinal axis. Each face 120, 130 may thus be a semi-circle.

To correct for the possibility of unequal acoustic energy being launched (or received) by the acoustic transducer into (or from) medium 102 compared to medium 103 (as when transducer 150 does not evenly straddle the two solid cylinder halves), it is possible to initially correct for this effect by using a low-pressure gas (air) or a vacuum as the immersion fluid and then taking a ratio of the reflected amplitudes. Because the impedance of air is significantly less than $Z_2$ or $Z_3$, the reflected amplitudes should be substantially the same (approximately 100 percent), unless the launched (or received) energies were different. A correction factor may then be derived for unequal launched (or received) energies, before subsequently applying the relevant equations.

In some implementations, the disclosed embodiments may be used as part of a drilling system. An example drilling system for use in conjunction with MWD and LWT is illustrated herein.

Figure 2:
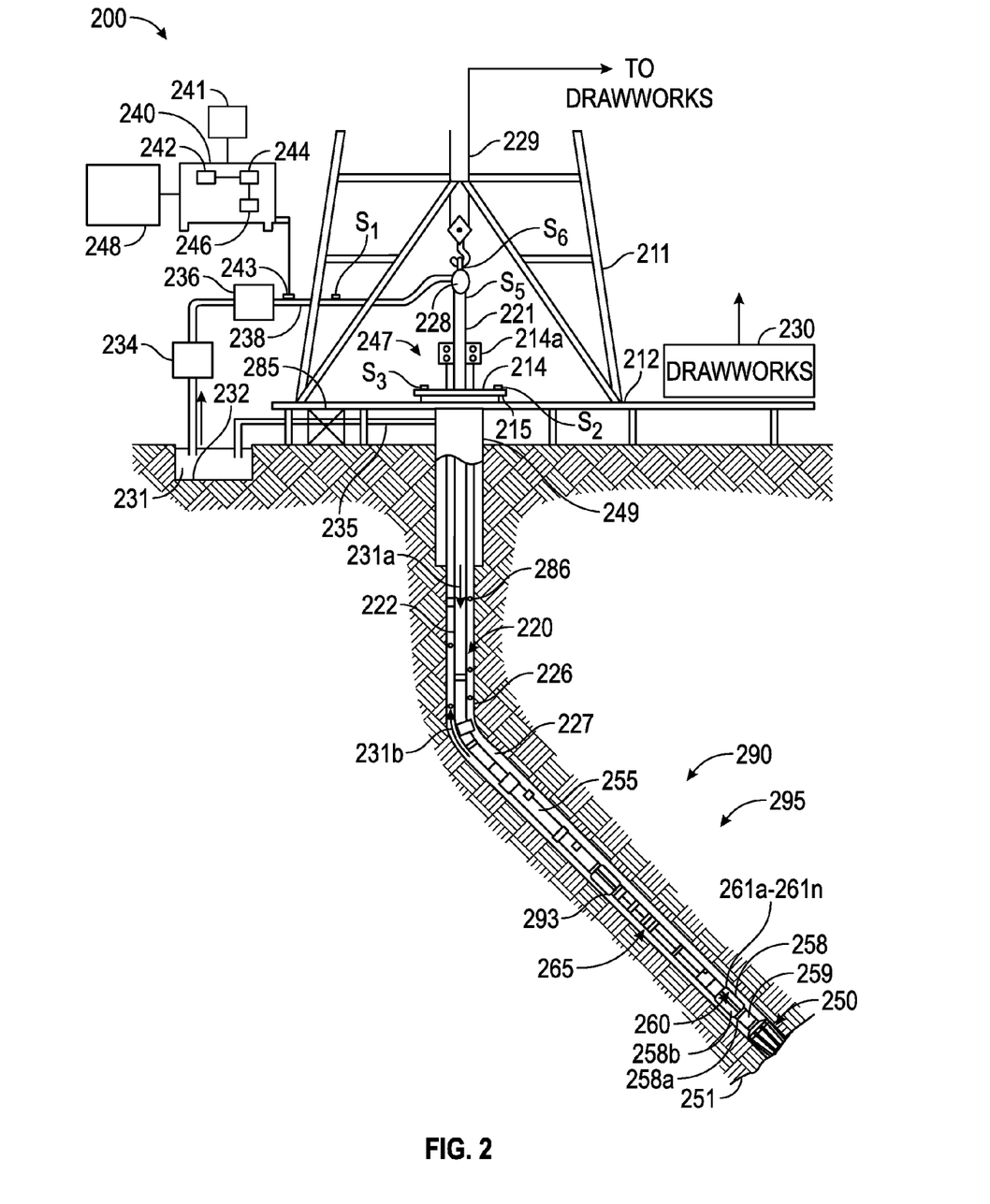
FIG. 2 is a schematic diagram of an exemplary drilling system 200 according to one embodiment of the disclosure.

FIG. 2 is a schematic diagram of an exemplary drilling system 200 according to one embodiment of the disclosure. FIG. 2 schematically illustrates a drilling system 200 configured to acquire information for downhole fluid analysis in a borehole intersecting a formation using a test apparatus; drilling system 200 includes a drill string 220 that includes a bottomhole assembly (BHA) 290 conveyed in a borehole 226. The drilling system 200 includes a conventional derrick 211 erected on a platform or floor 212 which supports a rotary table 214 that is rotated by a prime mover, such as an electric motor (not shown), at a desired rotational speed. A tubing (such as jointed drill pipe 222), having the drilling assembly 290, attached at its bottom end extends from the surface to the bottom 251 of the borehole 226. A drill bit 250, attached to drilling assembly 290, disintegrates the geological formations when it is rotated to drill the borehole 226. The drill string 220 is coupled to a drawworks 230 via a Kelly joint 221, swivel 228 and line 229 through a pulley. Drawworks 230 is operated to control the weight on bit ("WOB"). The drill string 220 may be rotated by a top drive (not shown) instead of by the prime mover and the rotary table 214. Alternatively, a coiled-tubing may be used as the tubing 222. A tubing injector 214a may be used to convey the coiled-tubing having the drilling assembly attached to its bottom end. The operations of the drawworks 230 and the tubing injector 214a are known in the art and are thus not described in detail herein.

A suitable drilling fluid 231 (also referred to as the "mud") from a source 232 thereof, such as a mud pit, may be circulated under pressure through the drill string 220 by a mud pump 234. The drilling fluid 231 passes from the mud pump 234 into the drill string 220 via a desurger 236 and the fluid line 238. The drilling fluid 231a from the drilling tubular discharges at the borehole bottom 251 through openings in the drill bit 250. The returning drilling fluid 231b circulates uphole through the annular space 227 between the drill string 220 and the borehole 226 and returns to the mud pit 232 via a return line 235 and drill cutting screen 285 that removes the drill cuttings 286 from the returning drilling fluid 231b. A sensor S1 in line 238 provides information about the fluid flow rate. A surface torque sensor S2 and a sensor S3 associated with the drill string 220 respectively provide information about the torque and the rotational speed of the drill string 220. Tubing injection speed is determined from the sensor S5, while the sensor S6 provides the hook load of the drill string 220.

Well control system 247 is placed at the top end of the borehole 226. The well control system 247 includes a surface blow-out-preventer (BOP) stack 215 and a surface choke 249 in communication with a wellbore annulus 227. The surface choke 249 can control the flow of fluid out of the borehole 226 to provide a back pressure as needed to control the well.

In some applications, the drill bit 250 is rotated by only rotating the drill pipe 222. However, in many other applications, a downhole motor 255 (mud motor) disposed in the BHA 290 also rotates the drill bit 250. The rate of penetration (ROP) for a given BHA largely depends on the WOB or the thrust force on the drill bit 250 and its rotational speed.

A surface control unit or controller 240 receives signals from the downhole sensors and devices via a sensor 243 placed in the fluid line 238 and signals from sensors S1-S6 and other sensors used in the system 200 and processes such signals according to programmed instructions provided to the surface control unit 240. The surface control unit 240 displays desired drilling parameters and other information on a display/monitor 241 that is utilized by an operator to control the drilling operations. The surface control unit 240 may be a computer-based unit that may include a processor 242 (such as a microprocessor), a storage device 244, such as a solid-state memory, tape or hard disc, and one or more computer programs 246 in the storage device 244 that are accessible to the processor 242 for executing instructions contained in such programs. The surface control unit 240 may further communicate with a remote control unit 248. The surface control unit 240 may process data relating to the drilling operations, data from the sensors and devices on the surface, data received from downhole, and may control one or more operations of the downhole and surface devices. The data may be transmitted in analog or digital form.

The BHA 290 may also contain formation evaluation sensors or devices (also referred to as measurement-while-drilling ("MWD") or logging-while-drilling ("LWD") sensors) determining resistivity, density, porosity, permeability, acoustic properties, nuclear-magnetic resonance properties, formation pressures, properties or characteristics of the fluids downhole and other desired properties of the formation 295 surrounding the BHA 290. Such sensors are generally known in the art and for convenience are generally denoted herein by numeral 265. The BHA 290 may further include a variety of other sensors and devices 259 for determining one or more properties of the BHA 290 (such as vibration, bending moment, acceleration, oscillations, whirl, stick-slip, etc.), drilling operating parameters (such as weight-on-bit, fluid flow rate, pressure, temperature, rate of penetration, azimuth, tool face, drill bit rotation, etc.).

The BHA 290 may include a steering apparatus or tool 258 for steering the drill bit 250 along a desired drilling path. In one aspect, the steering apparatus may include a steering unit 260, having a number of force application members 261a-261n. The force application members may be mounted directly on the drill string, or they may be at least partially integrated into the drilling motor. In another aspect, the force application members may be mounted on a sleeve, which is rotatable about the center axis of the drill string. The force application members may be activated using electro-mechanical, electro-hydraulic or mud-hydraulic actuators. In yet another embodiment the steering apparatus may include a steering unit 258 having a bent sub and a first steering device 258a to orient the bent sub in the wellbore and the second steering device 258b to maintain the bent sub along a selected drilling direction. The steering unit 258, 260 may include near-bit inclinometers and magnetometers.

The drilling system 200 may include sensors, circuitry and processing software and algorithms for providing information about desired drilling parameters relating to the BHA, drill string, the drill bit and downhole equipment such as a drilling motor, steering unit, thrusters, etc. Many current drilling systems, especially for drilling highly deviated and horizontal wellbores, utilize coiled-tubing for conveying the drilling assembly downhole. In such applications a thruster may be deployed in the drill string 290 to provide the required force on the drill bit.

Exemplary sensors for determining drilling parameters include, but are not limited to drill bit sensors, an RPM sensor, a weight on bit sensor, sensors for measuring mud motor parameters (e.g., mud motor stator temperature, differential pressure across a mud motor, and fluid flow rate through a mud motor), and sensors for measuring acceleration, vibration, whirl, radial displacement, stick-slip, torque, shock, vibration, strain, stress, bending moment, bit bounce, axial thrust, friction, backward rotation, BHA buckling, and radial thrust. Sensors distributed along the drill string can measure physical quantities such as drill string acceleration and strain, internal pressures in the drill string bore, external pressure in the annulus, vibration, temperature, electrical and magnetic field intensities inside the drill string, bore of the drill string, etc. Suitable systems for making dynamic downhole measurements include COPILOT, a downhole measurement system, manufactured by BAKER HUGHES INCORPORATED.

The drilling system 200 can include one or more downhole processors at a suitable location such as 293 on the BHA 290. The processor(s) can be a microprocessor that uses a computer program implemented on a suitable non-transitory computer-readable medium that enables the processor to perform the control and processing. The non-transitory computer-readable medium may include one or more ROMs, EPROMs, EAROMs, EEPROMs, Flash Memories, RAMs, Hard Drives and/or Optical disks. Other equipment such as power and data buses, power supplies, and the like will be apparent to one skilled in the art. In one embodiment, the MWD system utilizes mud pulse telemetry to communicate data from a downhole location to the surface while drilling operations take place. The surface processor 242 can process the surface measured data, along with the data transmitted from the downhole processor, to evaluate formation lithology. While a drill string 220 is shown as a carrier (conveyance device) for sensors 265, it should be understood that embodiments of the present disclosure may be used in connection with tools conveyed via rigid (e.g. jointed tubular or coiled tubing) as well as non-rigid (e.g. wireline, slickline, e-line, etc.) conveyance systems. The drilling system 200 may include a bottomhole assembly and/or sensors and equipment for implementation of embodiments of the present disclosure on either a drill string or a wireline.

A point of novelty of the system illustrated in FIG. 2 is that the surface processor 242 and/or the downhole processor 293 are configured to perform certain methods (discussed below) that are not in the prior art. Surface processor 242 or downhole processor 293 may be configured to control components of the drilling system 200. Surface processor 242 or downhole processor 293 may be configured to control sensors described above and to estimate a parameter of interest according to methods described herein. Control of these components may be carried out using one or more models using methods described below. Control of these devices, and of the various processes of the drilling system generally, may be carried out in a completely automated fashion or through interaction with personnel via notifications, graphical representations, user interfaces and the like. Reference information accessible to the processor may also be used.

More specifically, drill string 220 (or BHA 290) may include an apparatus for estimating one or more parameters of the downhole fluid. For convenience, such apparatus may be denoted by numeral 259 or 265, and may comprise device 100 or other devices or tools in accordance with embodiments of the present disclosure. In some general embodiments, surface processor 242, downhole processor 293, or other processors (e.g. remote processors) may be configured to use the apparatus to produce information indicative of the downhole fluid, such as, for example, drilling fluid. One of the processors may also be configured to estimate from the information a parameter of interest of the downhole fluid.

In some embodiments, drill string 220 may include an acoustic logging apparatus configured for evaluating the cement bond occupying the annular space between the casing and the borehole wall, as described in greater detail below with reference to FIG. 4. For convenience, such apparatus may be denoted by numeral 259 or 265. In some general embodiments, surface processor 242, downhole processor 293, or other processors (e.g. remote processors) may be configured to use the acoustic logging apparatus to produce information indicative of the properties of the cement bond.

In some embodiments, processors may include electromechanical and/or electrical circuitry configured to control one or more components of the tool apparatus. In other embodiments, processors may use algorithms and programming to receive information and control operation of the apparatus. Therefore, processors may include an information processor that is in data communication with a data storage medium and a processor memory. The data storage medium may be any standard computer data storage device, such as a USB drive, memory stick, hard disk, removable RAM, EPROMs, EAROMs, flash memories and optical disks or other commonly used memory storage system known to one of ordinary skill in the art including Internet based storage. The data storage medium may store one or more programs that when executed causes information processor to execute the disclosed method(s). Herein, "information" may include raw data, processed data, analog signals, and digital signals.

Figure 3:
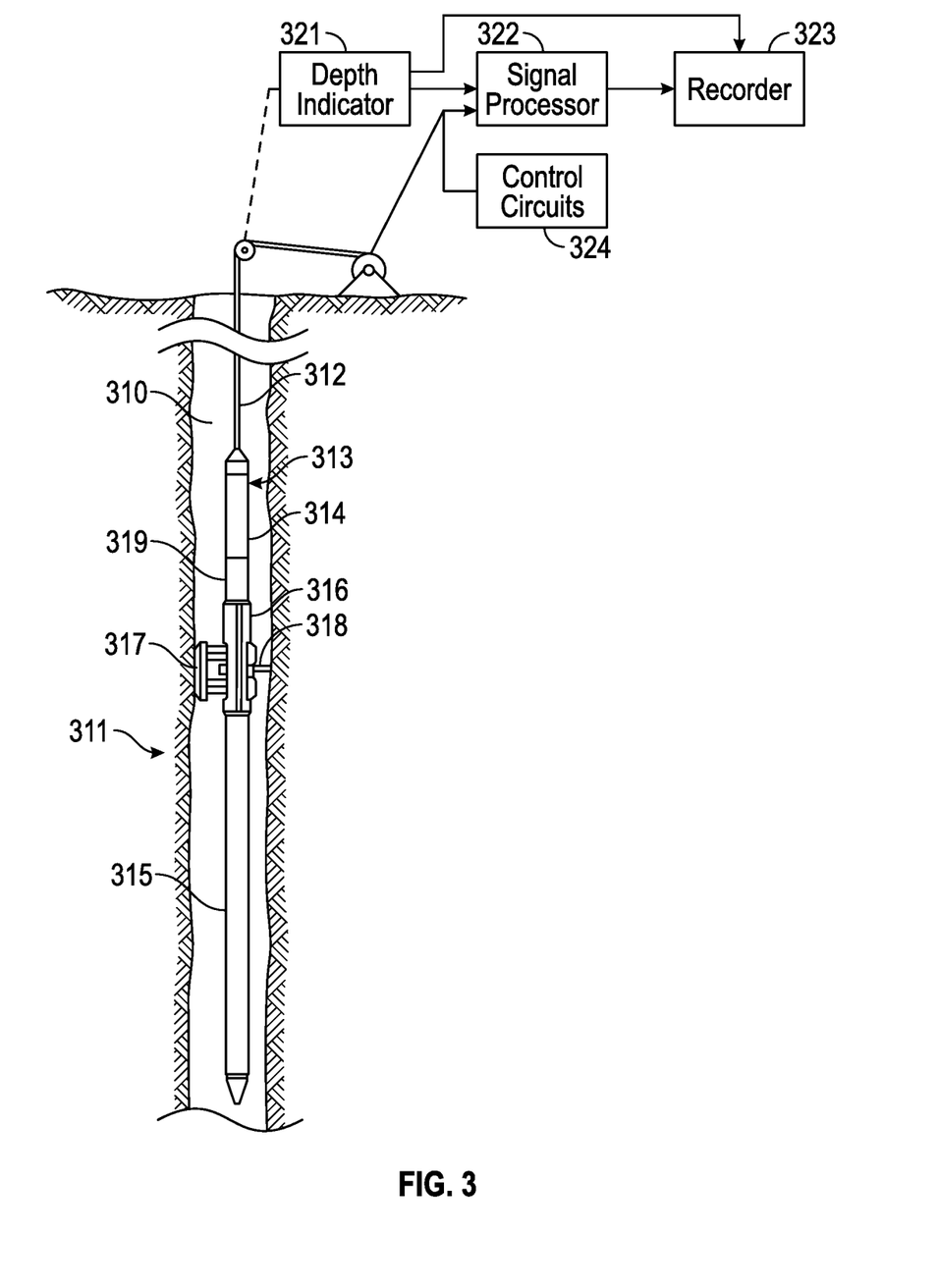
FIG. 3 illustrates a wireline tool in accordance with embodiments of the present disclosure in communication with the formation.

FIG. 3 illustrates a tool in accordance with embodiments of the present disclosure in communication with the formation. Borehole 310 intersects a portion of the earth formation 311. Disposed within the borehole 310 by means of a carrier 312 is a sampling and measuring instrument 313. Carrier 312 may be a drill string, coiled tubing, a slickline, an e-line, a wireline, etc. The sampling and measuring instrument includes hydraulic power system 314, a fluid sample storage section 315 and a sampling mechanism section 316. Sampling mechanism section 316 includes selectively extensible well engaging pad member 317, a selectively extensible fluid admitting sampling probe member 318 and bi-directional pumping member 319. Specific configuration of the components with respect to one another may vary.

In operation, sampling and measuring instrument 313 is positioned within borehole 310 via conveyance device 312 (e.g., by winding or unwinding cable 312 from a hoist (not shown)). Depth information from a depth indicator 321 is coupled to signal processor 322 and recorder 323 when instrument 313 is disposed adjacent an earth formation of interest. Control signals from control circuitry 324 are transmitted through electrical conductors contained within conveyance device 312 to instrument 313. Any or all of signal processor 322, control circuitry 324 and recorder 323 may be implemented with one more processors.

Electrical control signals activate an operational hydraulic pump within the hydraulic power system 314 shown, which provides hydraulic power causing the well engaging pad member 317 and the fluid admitting member 318 to move laterally from instrument 313 into engagement with the earth formation 311 and the bi-directional pumping member 319. Fluid admitting member or sampling probe 318 can then be placed in fluid communication with the earth formation 311, such as, for example, via electrical control signals from control circuits 324 selectively activating solenoid valves within instrument 313 for the taking of a sample of connate fluids contained in the earth formation of interest, or via other actuation techniques.

Figure 4:
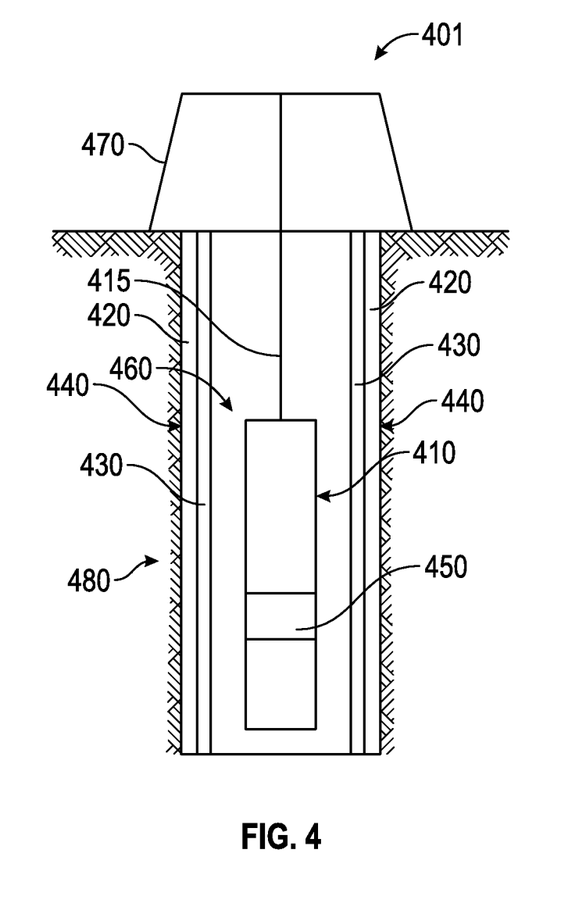
FIG. 4 illustrates an acoustic logging tool in accordance with embodiments of the present disclosure.

FIG. 4 illustrates an acoustic logging tool in accordance with embodiments of the present disclosure. The tool 410 is configured to be conveyed in a borehole intersecting a formation 480. The borehole wall 440 is lined with casing 430 filled with a downhole fluid 460, such as, for example, drilling fluid. Cement 420 fills the annulus between the borehole wall 440 and the casing 430. In one illustrative embodiment, the tool 410 may contain a sensor unit 450, including, for example, one or more acoustic transmitters and receivers (e.g., tranducers), configured for evaluation of the cement bond existing between the system of the casing 430, the borehole wall 440, and the cement 420 according to known techniques. For example, electronics in the tool 410, at the surface, or elsewhere in system 401 (e.g., at least one processor) may be configured to use acoustic measurements to determine properties of the cement bond using known techniques, such as, for example, analysis of casing resonance.

The system 401 may include a conventional derrick 470. A conveyance device (carrier 415) which may be rigid or non-rigid, may be configured to convey the downhole tool 410 into wellbore 440 in proximity to formation 480. The carrier 415 may be a drill string, coiled tubing, a slickline, an e-line, a wireline, etc. Downhole tool 410 may be coupled or combined with additional tools (e.g., some or all the information processing system of FIG. 2 or 3). Thus, depending on the configuration, the tool 410 may be used during drilling and/or after the wellbore (borehole) 440 has been formed. While a land system is shown, the teachings of the present disclosure may also be utilized in offshore or subsea applications. The carrier 415 may include embedded conductors for power and/or data for providing signal and/or power communication between the surface and downhole equipment. The carrier 415 may include a bottom hole assembly, which may include a drilling motor for rotating a drill bit.

For convenience, certain definitions are now presented. The term "acoustic signal" relates to the pressure amplitude versus time of a sound wave or an acoustic wave traveling in a medium that allows propagation of such waves. In one embodiment, the acoustic signal can be a pulse. The term "acoustic transducer" relates to a device for transmitting (i.e., generating) an acoustic signal or receiving an acoustic signal. When receiving the acoustic signal in one embodiment, the acoustic transducer converts the energy of the acoustic signal into electrical energy. The electrical energy has a waveform that is related to a waveform of the acoustic signal.

The term "carrier" (or "conveyance device") as used above means any device, device component, combination of devices, media and/or member that may be used to convey, house, support or otherwise facilitate the use of another device, device component, combination of devices, media and/or member. Exemplary non-limiting carriers include drill strings of the coiled tube type, of the jointed pipe type and any combination or portion thereof. Other carrier examples include casing pipes, wirelines, wireline sondes, slickline sondes, drop shots, downhole subs, BHA's, drill string inserts, modules, internal housings and substrate portions thereof, self-propelled tractors. As used above, the term "sub" refers to any structure that is configured to partially enclose, completely enclose, house, or support a device. The term "information" as used above includes any form of information (Analog, digital, EM, printed, etc.). The term "processor" herein includes, but is not limited to, any device that transmits, receives, manipulates, converts, calculates, modulates, transposes, carries, stores or otherwise utilizes information. A processor refers to any circuitry performing the above, and may include a microprocessor, resident memory, and/or peripherals for executing programmed instructions, application specific integrated circuits (ASICs), field programmable gate arrays (FPGAs), or any other circuitry configured to execute logic to perform methods as described herein. Fluid, as described herein, may refer to a liquid, a gas, a mixture, and so on. Predicted formation permeability and predicted formation mobility refer to values predicted for the formation and used to estimate the correction factor. Predicted values may be predicted from lithology, estimated from other estimation techniques, obtained by analogy, and so on, but are distinguished from parameters of interest estimating according to the methods disclosed herein.

Non-limiting examples of downhole fluids include drilling fluids, return fluids, formation fluids, production fluids containing one or more hydrocarbons, oils and solvents used in conjunction with downhole tools, water, brine, engineered fluids, and combinations thereof. The BHA may contain a formation test apparatus according to the present disclosure, which will be described in greater detail below.

While the disclosure has been described with reference to example embodiments, it will be understood that various changes may be made and equivalents may be substituted for elements thereof without departing from the scope of the disclosure. In addition, many modifications will be appreciated to adapt a particular instrument, situation or material to the teachings of the disclosure without departing from the essential scope thereof. Further embodiments may include direct measurement wireline embodiments, drilling embodiments employing a sample chamber, LWT tools, including drop subs and the like, and so on. While the present disclosure is discussed in the context of a hydrocarbon producing well, it should be understood that the present disclosure may be used in any borehole environment (e.g., a geothermal well) with any type of downhole fluid.

While the foregoing disclosure is directed to particular embodiments, various modifications will be apparent to those skilled in the art. It is intended that all variations be embraced by the foregoing disclosure.

What is claimed is:

1. A method of estimating a parameter of interest of a downhole fluid using an acoustic assembly comprising at least two solid acoustic transmission media, wherein a first media of the at least two solid acoustic transmission media has an acoustic impedance that is different than an acoustic impedance of a second media of the at least two solid acoustic transmission media, and wherein the first media and the second media each have a corresponding face immersed in the downhole fluid, the method comprising:
   using a reflection of a single longitudinal acoustic pulse from a solid-liquid interface at the corresponding face of the first media and the second media to estimate the parameter of interest.

2. The method of claim 1, wherein the acoustic pulse is propagated within the at least two solid acoustic transmission media.

3. The method of claim 1 wherein the first media has a sound speed that is different than a sound speed of the second media.

4. The method of claim 3 wherein the sound speed and the acoustic impedance of the first media and the sound speed and the acoustic impedance of the second media are each different than a sound speed and an acoustic impedance of the fluid.

5. The method of claim 1, comprising estimating the parameter of interest independently of a time of flight in the downhole fluid of the acoustic pulse and any other acoustic pulses.

6. The method of claim 1, further comprising transmitting the acoustic pulse using an acoustic transducer.

7. The method of claim 6, using the acoustic transducer to transmit the acoustic pulse through a corresponding second face of each of the first media and the second media.

8. The method of claim 7, wherein the acoustic pulse is transmitted through the corresponding second face of each of the first media and the second media simultaneously.

9. The method of claim 7, wherein the second face is not in contact with the downhole fluid.

10. The method of claim 7, wherein the acoustic transducer is not in contact with the downhole fluid.

11. The method of claim 1, wherein the acoustic assembly comprises a right circular cylinder.

12. The method of claim 1, wherein each of the first media and the second media comprises a half-cylinder and wherein each face comprises a semicircle.

13. The method of claim 1, wherein the parameter of interest is at least one of: i) sound speed of the downhole fluid; ii) acoustic impedance of the downhole fluid; and iii) density of the downhole fluid.

14. An apparatus for estimating a parameter of interest of a downhole fluid, the apparatus comprising:
   a carrier configured to be conveyed into a borehole;
   a logging tool mounted on the carrier, the logging tool including an acoustic assembly comprising at least two solid acoustic transmission media, wherein a first media of the at least two solid acoustic transmission media has an acoustic impedance that is different than an acoustic impedance of a second media of the at least two solid acoustic transmission media, and wherein the logging tool is configured such that when the borehole is filled with downhole fluid, the first media and the second media each have a corresponding face immersed in the downhole fluid; and a processor configured to use a reflection of a single longitudinal acoustic pulse from the solid-liquid interface at the corresponding face of the first media and the second media to estimate the parameter of interest.

* * * * *